(12) United States Patent
Matsuno

(10) Patent No.: US 6,556,911 B2
(45) Date of Patent: Apr. 29, 2003

(54) ROAD FRICTION COEFFICIENT ESTIMATING APPARATUS AND VEHICLE EQUIPPED WITH ROAD FRICTION COEFFICIENT ESTIMATING APPARATUS

(75) Inventor: Koji Matsuno, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/883,679

(22) Filed: Jun. 18, 2001

(65) Prior Publication Data

US 2002/0011093 A1 Jan. 31, 2002

(30) Foreign Application Priority Data

Jun. 29, 2000 (JP) .................................. 2000-197205

(51) Int. Cl.$^7$ .............................. B62D 7/15; B62D 6/00; B60T 8/00
(52) U.S. Cl. ........................ 701/80; 701/41; 180/422; 303/150
(58) Field of Search ............................... 701/1, 80, 41, 701/82, 90; 180/422, 412, 197, 415; 303/150, 166; 73/146, 104, 8, 9

(56) References Cited

U.S. PATENT DOCUMENTS

| | | | | |
|---|---|---|---|---|
| 4,909,073 A | * | 3/1990 | Takahashi et al. | ............. 73/146 |
| 4,964,481 A | * | 10/1990 | Sano et al. | .................. 180/140 |
| 5,020,619 A | * | 6/1991 | Kanazawa et al. | .......... 180/140 |
| 5,365,439 A | * | 11/1994 | Momose et al. | ........ 364/424.05 |
| 5,636,121 A | * | 6/1997 | Tsuyama et al. | ........ 364/426.01 |
| 6,079,801 A | * | 6/2000 | Zittlau | .......................... 303/150 |
| 6,184,637 B1 | * | 2/2001 | Yamawaki et al. | .......... 318/432 |
| 6,244,372 B1 | * | 6/2001 | Sakamaki et al. | ........... 180/422 |

FOREIGN PATENT DOCUMENTS

| | | |
|---|---|---|
| JP | 6-221968 | 8/1994 |
| JP | 11-287749 | 10/1999 |

* cited by examiner

Primary Examiner—Tan Q. Nguyen
Assistant Examiner—Dalena Tran
(74) Attorney, Agent, or Firm—Frishauf, Holtz, Goodman & Chick, P.C.

(57) ABSTRACT

A slip angle calculating unit calculates a slip angle of a vehicle body corresponding to a steering wheel angle and a vehicle speed, based on a vehicle wheel angle and the vehicle speed, by an observer of a preset vehicle motion model under a motion equation of a vehicle. A front wheel slip angle calculating unit calculates a front wheel slip angle based on the steering wheel angle, a vehicle speed, a yaw rate, and the calculated vehicle body slip angle. A self-aligning torque calculating unit calculates the self-aligning torque based on the hydraulic chamber pressure of the left side and the hydraulic chamber pressure of the right side in a power cylinder. The vehicle speed, an estimated front wheel slip angle, and the self-aligning torque are inputted to a road friction coefficient setting unit, and the road friction coefficient setting unit sets a road friction coefficient by referring to a map based on the input to output the set value. A road friction coefficient is estimated in wide ranges while reducing noises of sensors.

19 Claims, 7 Drawing Sheets

ROAD FRICTION COEFFICIENT ESTIMATING APPARATUS AND VEHICLE EQUIPPED WITH ROAD FRICTION COEFFICIENT ESTIMATING APPARATUS

BACKGROUND OF THE INVENTION

1. Field of the Invention

The present invention relates to a road friction coefficient estimating apparatus for precisely estimating a road friction coefficient in a wide driving range and a vehicle equipped with the road friction coefficient estimating apparatus.

2. Description of the Related Art

In recent years, various control technologies have been proposed and put into practical use with respect to traction controls, braking controls, or torque distribution controls for a vehicle. In these technologies, many apparatuses use a road friction coefficient for calculating a necessary control parameter or correcting thereof, and it is necessary to precisely estimate the road friction coefficient in order to securely perform the control.

Among such technologies for estimating the road friction coefficient, there is the one focused on the fact that magnitude of a self-aligning torque for a slip angle of a tire changes according to the road friction coefficient. For example, Japanese Unexamined Patent Application No.11-287749 discloses a device to estimate the road friction coefficient based on a steering wheel angle and a steering torque.

Further, for example, Japanese Unexamined Patent Application No. 6-221968 discloses a device to estimate the road friction coefficient based on a cornering force of a tire and a self-aligning torque.

However, in the former prior art mentioned above, there is a problem that a front wheel slip angle can not be detected with a steering wheel angle so that conditions enabling the detection of the road friction coefficient are limited, and thereby it is difficult to precisely estimate the road friction coefficient in a wide driving range.

Whereas, in the latter prior art mentioned above, a differential value of a sensor signal such as a differential value of a yaw rate at the time of detecting cornering force is used so that there is a problem of sensor noise, and thereby it is difficult to precisely estimate the road friction coefficient.

SUMMARY OF THE INVENTION

In view of the aforementioned, it is an object of the present invention to provide a road friction coefficient estimating apparatus which is able to estimate a road friction coefficient precisely in a wide driving range while reducing noise of a sensor, and a vehicle equipped with the road friction coefficient estimating apparatus.

To attain the object, the road friction coefficient estimating apparatus of the present invention for estimating the road friction coefficient on the road, comprising self-aligning torque detecting means for detecting a self-aligning torque of a steered wheel, steered wheel slip angle detecting means for detecting a slip angle of the steered wheel by inputting a detected value of a vehicle motion parameter to an observer formed by a motion model of a vehicle, and road friction coefficient setting means for setting a road friction coefficient based on the relationship between the self-aligning torque and the steered wheel slip angle.

And the road friction coefficient estimating apparatus of the present invention for estimating the road friction coefficient on the road, comprising a hydraulic power steering device for assisting a steering force by an oil pressure applied to a pair of hydraulic chambers of a power cylinder, oil pressure detecting means for detecting each oil pressure of the pair of hydraulic chambers, self-aligning torque detecting means for calculating a self-aligning torque based on a higher pressure of the pair of hydraulic chambers, steered wheel slip angle detecting means for detecting a slip angle of the steered wheel by inputting a detected value of a vehicle motion parameter to an observer formed by a motion model of a vehicle, and road friction coefficient setting means for setting a road friction coefficient based on the relationship between the self-aligning torque and the steered wheel slip angle.

Also the road friction coefficient estimating apparatus of the present invention for estimating the road friction coefficient on the road, comprising a hydraulic power steering device for assisting a steering force by an oil pressure applied to a pair of hydraulic chambers of a power cylinder, oil pressure detecting means for detecting each oil pressure of the pair of hydraulic chambers, self-aligning torque detecting means for calculating a self-aligning torque based on a difference of pressure in the pair of hydraulic chambers, steered wheel slip angle detecting means for detecting a slip angle of the steered wheel by inputting a detected value of a vehicle motion parameter to an observer formed by a motion model of a vehicle, and road friction coefficient setting means for setting a road friction coefficient based on the relationship between the self-aligning torque and the steered wheel slip angle.

And also, the road friction coefficient estimating apparatus of the present invention for estimating the road friction coefficient on the road, comprising an electric power steering device for assisting a steering force with an electric motor, torsion bar torque detecting means for detecting a torsion bar torque, motor current detecting means for detecting the driving current of the electric motor, self-aligning torque detecting means for calculating a self-aligning torque based on the torsion bar torque and the motor current, steered wheel slip angle detecting means for detecting a slip angle of the steered wheel by inputting a detected value of a vehicle motion parameter to an observer formed by a motion model of a vehicle, and road friction coefficient setting means for setting a road friction coefficient based on the relationship between the self-aligning torque and the steered wheel slip angle.

The above and other objects, features and advantages of the invention will become more clearly understood from the following description when taken in conjunction with the accompanying drawings.

DESCRIPTION OF THE PREFERRED EMBODIMENTS

Figure 1:
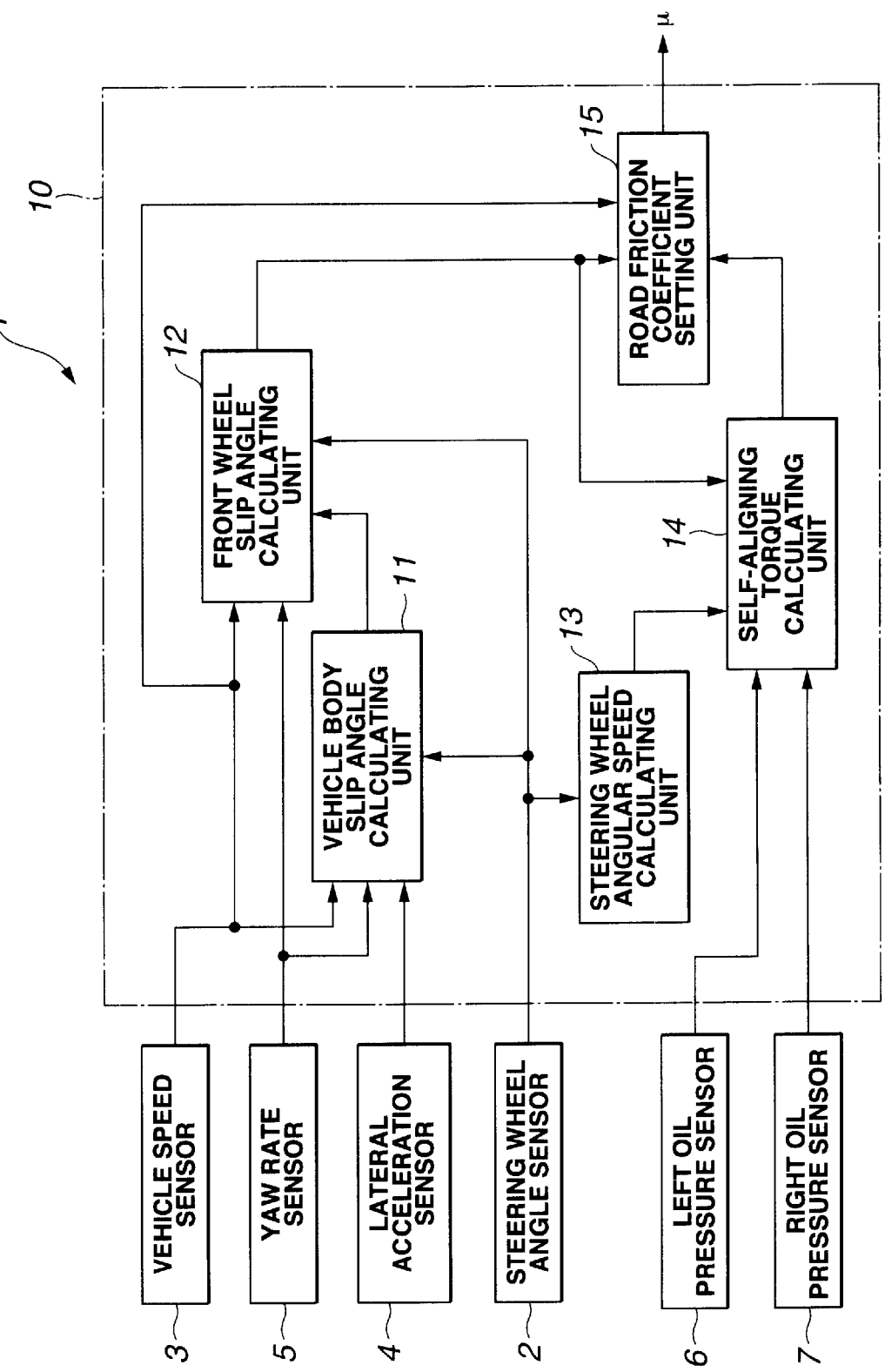
FIG. 1 is a function block diagram showing a structure of a road friction coefficient estimating apparatus according to a first embodiment of the present invention.

Below, a first embodiment of the present invention will be described referring to the drawings. In the first embodiment, as an example, a road friction coefficient estimating apparatus is explained. The road friction coefficient estimating apparatus is equipped to a vehicle having a known hydraulic power steering device to assist steering force of a driver by introducing an oil pressure generated by an oil pump into a pair of hydraulic chambers (left and right) of a power cylinder provided in a steering gear box.

In FIG. 1, numeral 1 denotes a road friction coefficient estimating apparatus for estimating a road friction coefficient. A steering wheel angle sensor 2, a vehicle speed sensor 3, a lateral acceleration sensor 4, and a yaw rate sensor 5 are connected to a control unit 10 of the road friction coefficient estimating apparatus 1 and a steering wheel angle θH, a vehicle speed V, a lateral acceleration $d^2y/dt^2$, a yaw rate (yaw angular speed) dφ/dt respectively from the steering wheel angle sensor 2, the vehicle sensor 3, the lateral acceleration sensor 4, and the yaw rate sensor 5 are inputted to the control unit 10.

An oil pressure sensor 6 on the left side and an oil pressure sensor 7 on the right side, as oil pressure detecting means for detecting an oil pressure in a hydrauric chamber on the left side and a hydrauric chamber on the right side of a power cylinder in a hydrauric power steering apparatus (not shown) respectively, are connected to the control unit 10 of the road friction coefficient estimating apparatus 1, and an oil pressure PcL in the hydrauric chamber on the left side and an oil pressure Pcr in the hydrauric chamber on the right side are inputted to the control unit 10.

The control unit 10 of the road friction coefficient estimating apparatus 1 comprises a microcomputer and peripheral circuits thereof, that is, it mainly comprises a vehicle body slip angle calculating unit 11, a front wheel slip angle calculating unit 12, a steering wheel angular speed calculating unit 13, a self-aligning torque calculating unit 14, and a road friction coefficient setting unit 15.

A steering wheel angle θH from a steering wheel angle sensor 2 and a vehicle speed V from a vehicle speed sensor 3 are inputted to the vehicle body slip angle calculating unit 11. The vehicle body slip angle calculating unit 11 calculates a vehicle body slip angle corresponding to the detected steering wheel angle θH and the detected vehicle speed V by a vehicle motion model based on a preset motion equation of the vehicle, and outputs the calculated value to the front-wheel slip angle calculating unit 12.

Figure 3:
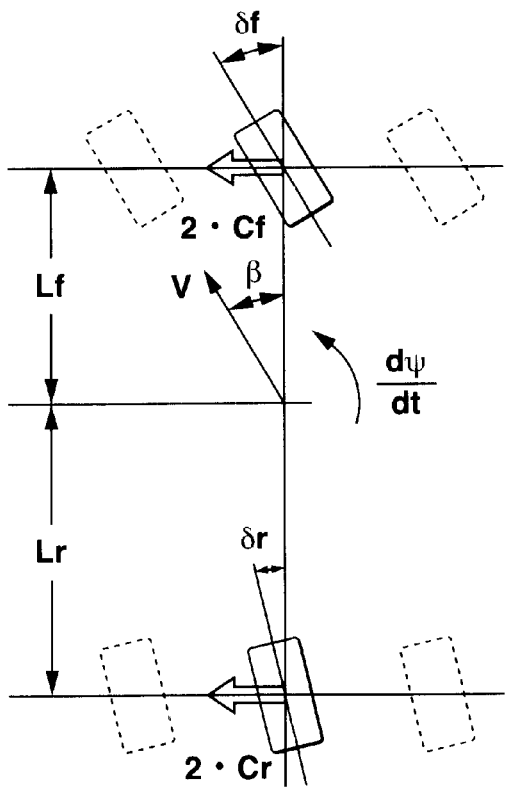
FIG. 3 is an explanatory diagram showing a two-wheel model of side motion in a vehicle according to the first embodiment of the present invention.

The motion equation of lateral motion for a vehicle is obtained by using the vehicle motion model in FIG. 3. A motion equation with respect to translation of a lateral direction of the vehicle is expressed as the following formula (1).

$$2 \cdot Cf + 2 \cdot Cr = M \cdot (d^2y/dt^2) \tag{1}$$

where Cf is cornering force of front wheel (single wheel), Cr is cornering force of rear wheel (single wheel), M is a vehicle body mass and $d^2y/dt^2$ is a lateral acceleration.

On the other hand, a motion equation with respect to a revolution motion around a center of gravity is expressed as the following formula (2).

$$2 \cdot Cf \cdot Lf - 2 \cdot Cr \cdot Lr = Iz \cdot (d^2\phi/dt^2) \tag{2}$$

where Lf is distance from the center of gravity to front wheel axle, Lr is distance from the center of gravity to rear wheel axle, Iz is yawing inertia moment of vehicle body and $d^2\phi/dt^2$ is yaw angular acceleration.

The lateral acceleration $d^2y/dt^2$ is expressed as the following formula (3).

$$(d^2y/dt^2) = V \cdot ((d\beta/dt) + (d\phi/dt)) \tag{3}$$

where β is vehicle body slip angle, and dβ/dt is vehicle body slip angular speed.

Therefore, the above formula (1) can be expressed as the following formula (4).

$$2 \cdot Cf + 2 \cdot Cr = M \cdot V \cdot ((d\beta/dt) + (d\phi/dt)) \tag{4}$$

Cornering force responds to a side slip angle of a tire which is almost a first-order lag, however, the response lag is ignored. When a linearization is performed using an equivalent cornering power incorporating characteristics of a suspension into the characteristics of the tire, the cornering force Cf and Cr are expressed as the following formulas (5) and (6).

$$Cf = Kf \cdot \alpha f \tag{5}$$

$$Cr = Kr \cdot \alpha r \tag{6}$$

where Kf is equivalent cornering power of the front wheel, Kr is equivalent cornering power of the rear wheel, αf is slip angle of the front wheel, and αr is slip angle of the rear wheel.

Considering roll and suspension influences in equivalent cornering powers Kf and Kr, a slip angle αf of a front wheel and a slip angle αr of the rear wheel can be simplified as following, by using the equivalent cornering powers Kf, Kr.

$$\alpha f = \delta f - (\beta + Lf \cdot (d\phi/dt)/V) \tag{7}$$
$$= (\theta H/n) - (\beta + Lf \cdot (d\phi/dt)/V)$$

$$\alpha r = \delta r - (\beta - Lr \cdot (d\phi/dt)/V) \tag{8}$$

where αf is front wheel angle, αr is rear wheel angle, δf is front wheel steering angle, δr is rear wheel steering angle, n is steering gear ratio.

As a result of the above motion equations, the following state equation (9) is obtained.

$$(dx(t)/dt) = A \cdot x(t) + B \cdot u(t) \quad x(t) = [\beta(d\phi/dt)]^T u(t) = [\theta H \delta r]^T \tag{9}$$

$$A = \begin{bmatrix} a11 & a12 \\ a21 & a22 \end{bmatrix}$$

-continued $$B = \begin{bmatrix} b11 & b12 \\ b21 & b22 \end{bmatrix}$$

a11=−2·(Kf+Kr)/(M·V)

a12=−1.0−2·(Lf·Kf−Lr·Kr)/(M·V²)

a21=−2·(Lf·Kf−Lr·Kr)/Iz a22=−2·(Lf²·Kf+Lr²·Kr)/Iz·V)

b11=2·Kf/(M·V·n)

b12=2·Kr/(M·V)

b21=2·Lf·Kf/Iz b22=−2·Lr·Kr/Iz

Figure 4:
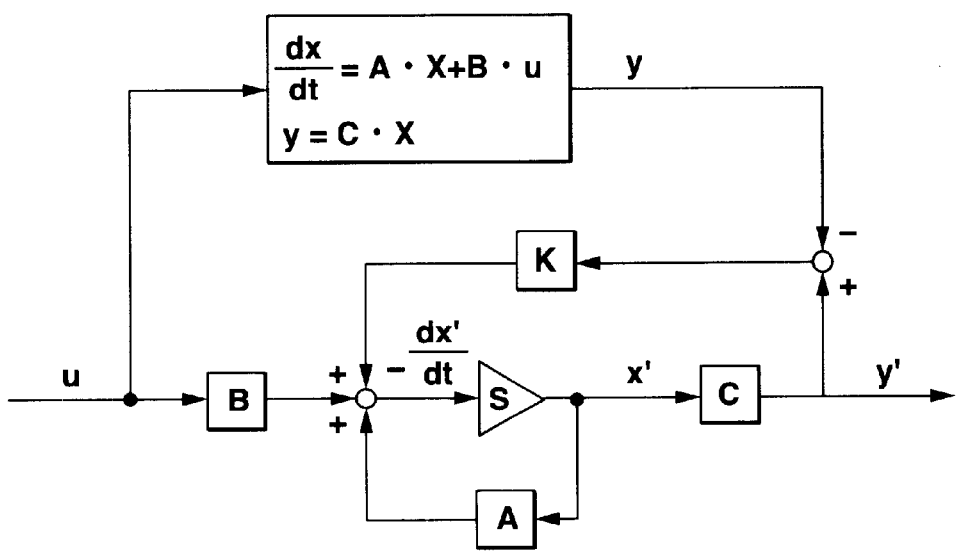
FIG. 4 is an explanatory diagram showing a structure of a general observer according to the first embodiment of the present invention.

The constitution of an observer to estimate the vehicle body slip angle is explained referring to FIG. 4.

When the output which can be measured (can be detected with a sensor) is expressed as the following formula (10), the constitution (structure) of the observer is expressed as the formula (11).

$$y(t)=C\cdot x(t) \tag{10}$$

$$(dx'(t)/dt)=(A-K\cdot C)\cdot x'(t)+K\cdot y(t)+B\cdot u(t) \tag{11}$$

or $$(dx'(t)/dt)=A\cdot x'(t)+B\cdot u(t)-K\cdot C\cdot (x'-x) \tag{12}$$

Here, ['] of x'(t) denotes an estimated value.

Figure 2:
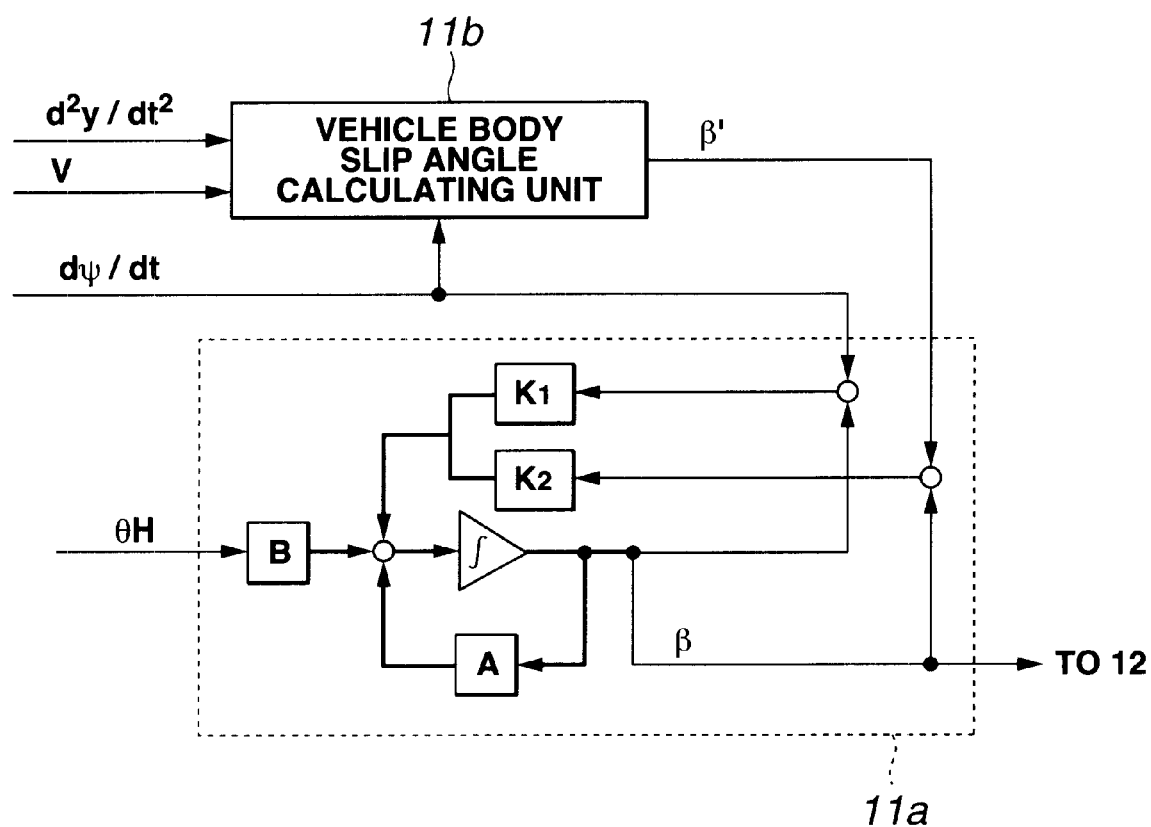
FIG. 2 is a function block diagram showing a structure of a vehicle body slip angle calculating unit according to the first embodiment of the present invention.

When the above formula (12) is adapted for the vehicle motion model because a value of C is the following matrix, $$C = \begin{bmatrix} 1 & 0 \\ 0 & 1 \end{bmatrix} \tag{13}$$

the formula (12) can be expressed as the following formula (14).

$$(dx'(t)/dt)=A\cdot x'(t)+B\cdot u(t)-K\cdot (x'-x) \tag{14}$$

where K is as follows:

$$K = \begin{bmatrix} k11 & k12 \\ k21 & k22 \end{bmatrix}$$

where in a case of setting K so that matrix (A−K·C) is stable matrix, that is, real part of eigen value of (A−K·C) is negative (left half part of complex), x'(t)→x(t) is ensured. Since u(t) is [θH δr]$^T$ and x(t) is [β(dφ/dt)]$^T$, an observer 11a in which only a front wheel steering angle δf changes is constituted such that the yaw rate and a vehicle body slip angle β are estimated based on the steering wheel angle θH as shown in FIG. 2. Here, in FIG. 2, 11a denotes an observer by a vehicle motion model with two degrees of freedom. Bold characters (K1, K2, A, B) and bold lines denote a matrix and a vector respectively.

Deviation between the estimated yaw rate and an actual yaw rate (from yaw rate sensor 5) is calculated by which the deviation (yaw rate deviation) is obtained. The deviation between the estimated vehicle body slip angle β and an actual vehicle body slip angle β' is calculated by which the deviation (vehicle body slip angle deviation) is obtained. The actual vehicle body slip angle β' is calculated in an actual vehicle body slip angle calculating unit 11b. The yaw rate deviation is multiplied by K1. The vehicle body slip angle deviation is multiplied by K2. The values multiplied as above are respectively subtracted from the sum of the product of the steering wheel angle θH by B, and the respective products of the estimated yaw rate by A and of the estimated vehicle slip angle β by A. Therefore, calculation for estimating the yaw rate and the vehicle body slip angle β is precisely performed by integrating the subtracted results respectively.

Sensor noises with a high frequent wave which can not be caused in the vehicle can be effectively extracted by using the vehicle motion model.

An actual vehicle body slip angle calculating unit 11b calculates the actual vehicle body slip angle β' necessary for the feedback of an observer 11a based on, not the sensor signal itself, but the following formula (15)

$$\beta'=\int((d^2y/dt^2)/V-(d\phi/dt))dt \tag{15}$$

The steering wheel angle θH from the steering wheel angle sensor 2, the vehicle speed V from the vehicle speed sensor 3, the yaw rate dφ/dt from the yaw rate sensor 5 and the estimated vehicle body slip angle β from the vehicle body slip angle calculating unit 11 are inputted to the front wheel slip angle calculating unit 12. The front wheel slip angle calculating unit 12 calculates the slip angle αf of a steered wheel, that is, a front wheel based on the aforementioned formula (7) and outputs the front wheel slip angle αf to the self-aligning torque calculating unit 14 and the road friction coefficient setting unit 15. In the first embodiment, a steered wheel slip angle detecting means comprises the vehicle body slip angle calculating unit 11 and the front wheel slip angle calculating unit 12.

The steering wheel angular speed calculating unit 13 is provided as steering speed detecting means and a signal from the steering wheel angle sensor 2 is inputted to the steering wheel angular speed calculating unit 13. The calculating unit 13 calculates the volume of changes of the steering wheel angle θH in a set time (a very short period of time) as a steering wheel angular speed dθH/dt and outputs the value to the self-aligning torque calculating unit 14.

The self-aligning torque calculating unit 14 is comprised, as the self-aligning torque detecting means, such that hydraulic chamber pressures PcL and Pcr on the left side and on the right side are respectively inputted from the oil pressure sensors 6 and 7 on the left side and on the right side of the power cylinder to the self-aligning torque calculating unit 14, the self-aligning torque calculating unit 14 calculates a self-aligning torque Tsa, and the self-aligning torque calculating unit 14 outputs the value to the road friction coefficient setting unit 15.

The steering wheel angular speed dθH/dt is inputted from the steering wheel angular speed calculating unit 13 and the front wheel slip angle αf is inputted from the front wheel slip angle calculating unit 12 to the self-aligning torque calculating unit 14.

Calculation of the self-aligning torque Tsa in the self-aligning torque calculating unit 14 is performed, for example, in any manner of the following formulas.

1.

$$Tsa=Pc\cdot Ac\cdot Ln \tag{16}$$

where Pc is the higher value between the left hydraulic chamber pressure PcL and the right hydraulic chamber pressure Pcr, Ac is a pressure receiving area of power cylinder, and Ln is a steering knuckle arm length (distance between a tie rod connecting point on wheel side and a king pin axle).

2.

$$Tsa=|Pc|\cdot Ac\cdot Ln \qquad (17)$$

where ΔPc is difference between the left hydraulic chamber pressure PcL and the right hydraulic chamber pressure Pcr.

3.

$$Tsa=(|Pc|-|d\theta H/dt|\cdot Cdt)\cdot Ac\cdot Ln \qquad (18)$$

where Cdt is coefficient to obtain pressure loss in hydraulic pipe and valve based on steering speed when calculation is carried out, in consideration of the steering wheel angular speed dθH/dt in the above formula (17).

4.

$$Tsa=Pp\cdot Ac\cdot Ln \qquad (19)$$

where a discharge pressure Pp of the oil pump has been detectable.

5.

$$Tsa=(Pc-|d\theta H/dt|\cdot Cdt)\cdot Ac\cdot Ln \qquad (20)$$

where Tsa is calculated in consideration of the steering wheel angular speed dθH/dt in the above formula (19).

The self-aligning torque calculating unit 14 compares the inputted front wheel slip angle αf with a threshold θc preset through experiments, etc. When it is judged that the front wheel slip angle αf is smaller than θc, and the error is large, the self-aligning torque calculating unit 14 stops the calculation of the self-aligning torque Tsa. The self-aligning torque Tsa can be, always, calculated in a precise range and a road friction coefficient μ can be precisely estimated.

The vehicle speed V from the vehicle speed sensor 3, the front wheel slip angle αf estimated by the observer from the front wheel slip angle calculating unit 12, and the self-aligning torque Tsa from the self-aligning torque calculating unit 14 are inputted to the road friction coefficient setting unit 15. And the road friction coefficient setting unit 15 is provided as the road friction coefficient setting means for setting the road friction coefficient μ based on these inputs to output the value.

Figure 5:
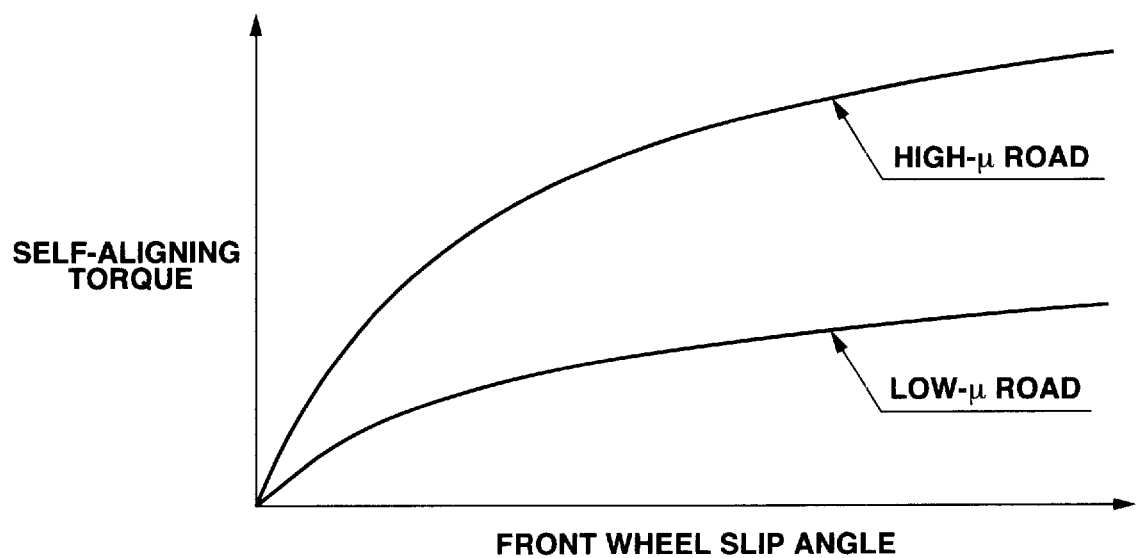
FIG. 5 is an explanatory characteristic map for a road friction coefficient of a front wheel slip angle and self-aligning torque according to the first embodiment of the present invention.

The road friction coefficient μ in the road friction setting unit 15 is basically set in accordance with a characteristics map for the road friction coefficient of a front-wheel slip angle and a self-aligning torque shown in FIG. 5, for example, in which the front wheel slip angle αf and a self-aligning torque Tsa are previously obtained through experiments or calculations.

The characteristics map for the road friction coefficient of the front wheel slip angle and the self-aligning torque is a map representing the characteristics of each the slip angle αf of each front wheel. The characteristics show that in a case where the front wheel slip angle αf is constant; the higher the road friction coefficient μ is, the larger the self-aligning torque Tsa is.

The road friction coefficient setting unit 15 is, therefore, constituted such that setting the road friction coefficient μ is prohibited when the vehicle speed V is very slow (lower than a preset threshold Vc), because a torque of the steering (when the wheel stopped on the road is steered) is highly effected, so that there is a possibility that a precise estimation becomes difficult.

Figure 6:
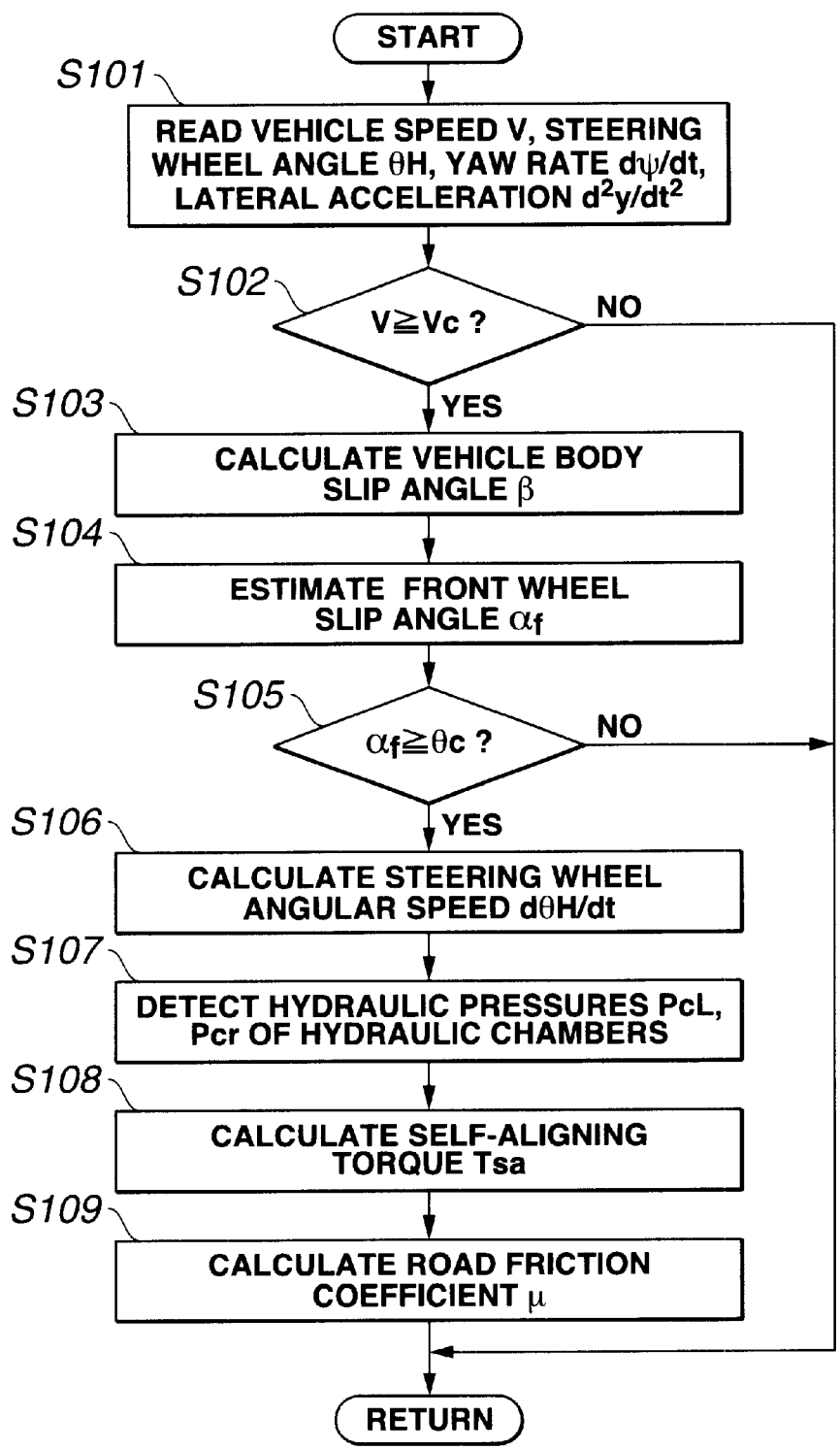
FIG. 6 is a flow chart for estimating a road friction coefficient according to the first embodiment of the present invention.

Next, the flow of the road friction coefficient estimating processing in the road friction coefficient estimating apparatus 1 is explained referring to FIG. 6. This program is executed at each predetermined time. At step (hereinafter referred to as "S") 101, the vehicle speed V from the vehicle speed sensor 2, the steering wheel angle θH from the steering wheel angle sensor 2, the yaw rate dφ/dt from the yaw rate sensor 5, and the lateral acceleration $d^2y/dt^2$ from the lateral acceleration sensor 4 are read, and then, at S102, whether the vehicle speed V is larger than or equal to the preset threshold Vc or not is judged.

When the vehicle speed V is smaller than the threshold Vc at S102, the road friction coefficient μ is not set and the program is ended (terminated) because an influence of the steering torque (when the wheel stopped on the road is steered) increases and there is a possibility that the precise estimation becomes difficult. On the other hand, when the vehicle speed V is larger than or equal to the threshold Vc, the routine proceeds to S103.

At S103, the vehicle body slip angle calculation unit 11 estimates the vehicle body slip angle β by the observer. And, at S104, the front wheel slip angle calculation unit 12 calculates the front wheel slip angle αf using the aforementioned formula (7) based on the vehicle body slip angle β estimated at S103.

Thereafter, at S105, whether the front wheel slip angle αf calculated at S104 is larger than or equal to the preset threshold θc or not is judged. When the front wheel slip angle αf is larger than or equal to the threshold θc, the routine proceeds to S106. When the front wheel slip angle αf is smaller than the threshold θc, it is judged that the error of the slip angle αf is large, and the road friction coefficient μ is not set and the program is ended (terminated).

After the routine proceeds from S105 to S106, the calculating unit 13 calculates the steering wheel angular speed dθH/dt at S106.

The routine proceeds to S107 and the hydraulic chamber pressure PcL and Pcr on the left side and on the right side are respectively inputted from the oil pressure sensors 6 and 7 on the left side and on the right side in the power cylinder.

The routine proceeds to S108 and the self-aligning torque calculating unit 14 calculates the self-aligning torque Tsa.

The routine proceeds to S109 and the road friction coefficient setting unit 15 sets the road friction coefficient μ, based on the front wheel slip angle αf and the self-aligning torque Tsa, referring to the characteristic map, for the road friction coefficient, of the front wheel slip angle and the self-aligning torque.

According to the first embodiment, since the road friction estimating apparatus detects the front wheel angle αf to set the road friction coefficient μ, the road friction coefficient μ can be estimated in a wide driving range.

Also, since the front wheel slip angle αf is detected using the observer, the road friction coefficient μ can be precisely estimated while reducing noises of sensors or cumulative errors.

Further, since the calculation of the self-aligning torque Tsa is possible in various manners, the self-aligning torque is superior in use.

Furthermore, since the road friction coefficient μ is not set when the error becomes large at the time of the slow vehicle speed V or the small front wheel slip angle αf, outputting the road friction coefficient μ with a large error can be prevented securely.

Next, a second embodiment of the present invention will be described. As an example, the road friction coefficient estimating apparatus equipped to the vehicle having a known electric power steering device is explained. The electric power steering device assists the steering force of the driver with an electric motor based on parameters of the torque which is yielded when the driver rotates the steering wheel (torsion bar torque), the electric current value of the electric motor, the vehicle speed and the like.

The structure and processing, with respect to the calculation of the self-aligning torque, differs from ones of the aforementioned first embodiment. The parts which are the same in the first embodiment are assigned the same symbols, and the detailed explanation thereof is omitted.

Figure 7:
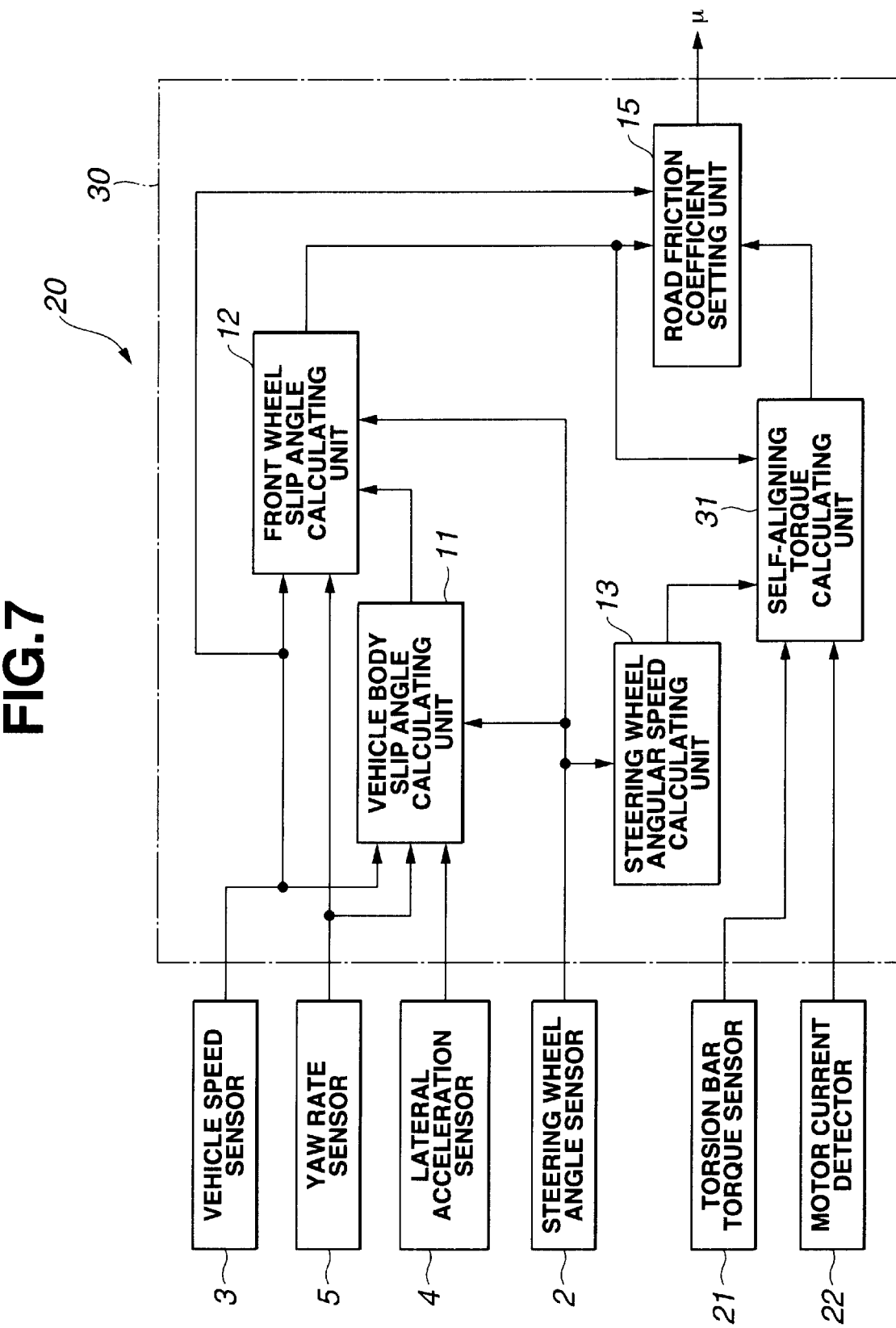
FIG. 7 is a function block diagram showing a structure of a road friction coefficient estimating apparatus according to a second embodiment of the present invention.

In FIG. 7, numeral 20 denotes the road friction coefficient estimating apparatus for estimating the road friction coefficient. The steering wheel angle sensor 2, the vehicle speed sensor 3, the lateral acceleration sensor 4, and the yaw rate sensor 5 are connected to a control unit 30 of the road friction coefficient estimating apparatus 20. And a steering wheel angle $\theta H$, a vehicle speed V, a lateral acceleration $d^2y/dt^2$ and a yaw rate (yaw angle speed) $d\phi/dt$ respectively from the steering wheel angle sensor 2, the vehicle speed sensor 3, the lateral acceleration sensor 4, and the yaw rate sensor 5 are inputted to the control unit 30.

A torsion bar torque Tt from a torsion bar torque sensor 21 as a torsion bar torque detecting means and a motor electric current value Ia from a motor electric current detector 22 as an electric current detecting means for detecting a driving current of an electric motor in an electric power steering device (not shown) are inputted to the control unit 30 of the road friction coefficient estimating apparatus 20.

The control unit 30 of the road friction coefficient estimating apparatus 20 comprises the microcomputer and the peripheral circuits thereof, that is, it mainly comprises the slip angle calculating unit 11, the front wheel slip angle calculating unit 12, the calculating unit 13, a self-aligning torque calculating unit 31 and the road friction coefficient setting unit 15.

The torsion bar torque Tt from the torque sensor 21 and the electric current value Ia from the electric current detector 22 are inputted to the self-aligning torque calculating unit 31. The self-aligning torque calculating unit 31 calculates a self-aligning torque Tsa based on the inputted values and outputs the value to the road friction coefficient setting unit 15. That is, the self-aligning torque calculating unit 31 is comprised as self-aligning torque detecting means.

A steering wheel angular speed $d\theta H/dt$ from the steering wheel angular speed calculating unit 13 and a front wheel slip angle $\alpha f$ from the front wheel slip angle calculating unit 12 are inputted to the self-aligning torque calculating unit 31.

The self-aligning torque Tsa in the self-aligning torque calculating unit 31 is calculated by, e.g., the following formula (21) or (22).

$$Tsa = |Tt \cdot Ct + Ia \cdot Ca| \cdot Ln \quad (21)$$

where Ct is the coefficient (effective diameter of pinion) which converts a torsion bar torque Tt into a rack thrust, and Ca is the coefficient which converts the electric current value Ia of the electric motor into the rack thrust.

When Tsa is calculated by the above formula (21) in consideration of the steering wheel angular speed $d\theta H/dt$, the formula is as follows:

$$Tsa = |Tt \cdot Ct + Ia \cdot Ca - Ip \cdot (d\theta H/dt)| \cdot Ln \quad (22)$$

where Ip is an inertia of the electric motor.

The electric current value Ia of the electric motor is used in the second embodiment, however, a target torque of the electric motor may be used therein.

The self-aligning torque calculating unit 31 compares the front wheel slip angle $\alpha f$ with a threshold $\theta c$ preset through experiments, etc. And it is judged that the front wheel slip angle $\alpha f$ is smaller than $\theta c$ and the error is large, the self-aligning torque calculating unit 31 stops the calculation of the self-aligning torque Tsa. In this way, the self-aligning torque Tsa can be, always, calculated in a highly precise range, and the road friction coefficient $\mu$ can be precisely estimated.

Figure 8:
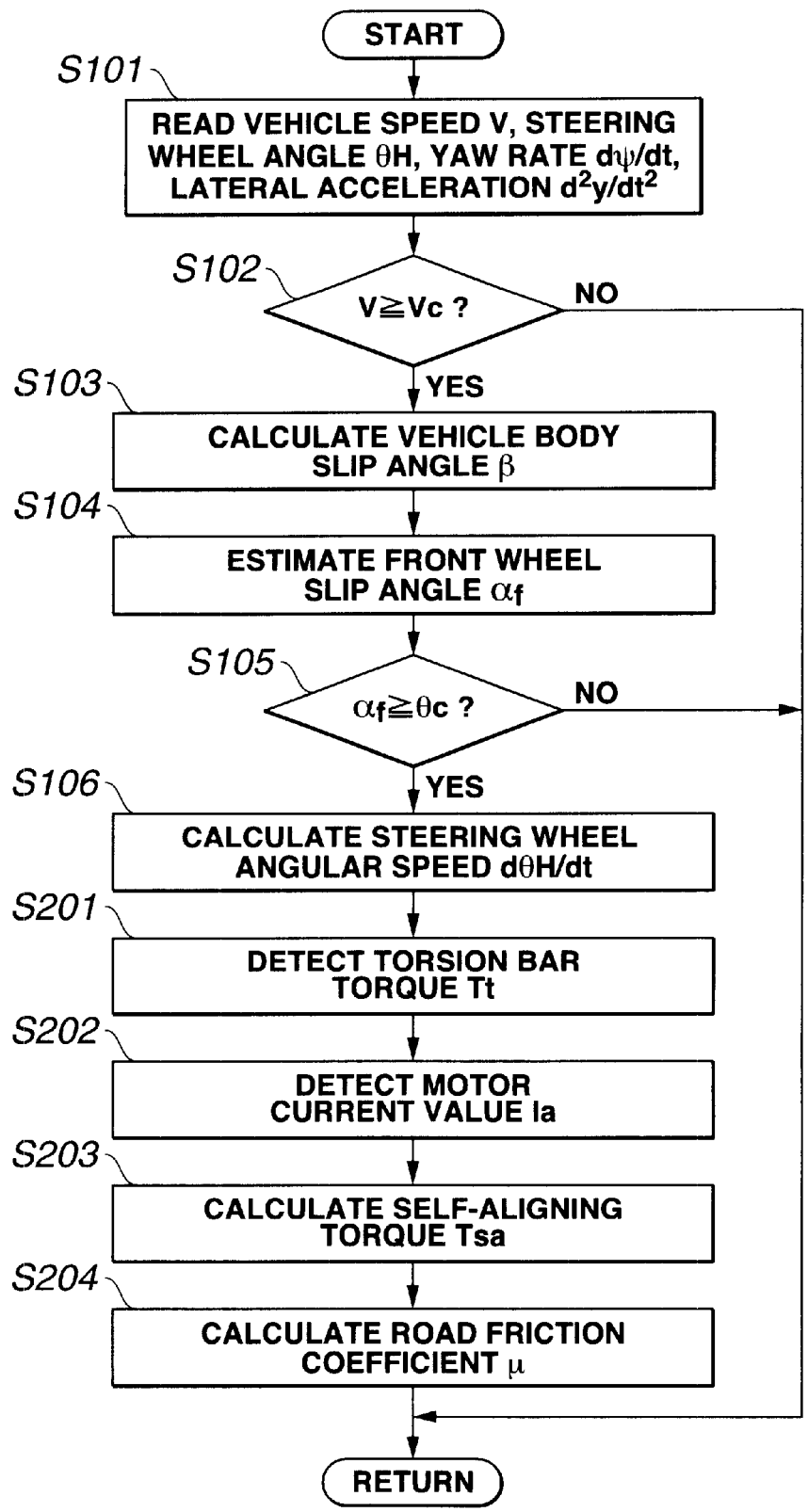
FIG. 8 is a flow chart for estimating a road friction coefficient according to the second embodiment of the present invention.

Next, the flow of the road friction coefficient estimation processing in a road friction coefficient estimating apparatus 20 is explained in a flow chart of FIG. 8. This program is executed per predetermined time. At S101 to S106, the program is processed in the same manner as the first embodiment. After the steering wheel angular speed calculating unit 13 calculates the steering wheel angular speed $d\theta H/dt$ at s106, the routine proceeds to S201.

At S201, the torsion bar torque Tt is detected by the torsion bar torque sensor 21. And then the routine proceeds to S202, and the motor electric current value Ia is detected by the motor electric current detector 22.

Thereafter, the routine proceeds to S203 and the self-aligning torque calculating unit 31 calculates the self-aligning torque Tsa.

The routine proceeds to S204 and the road friction coefficient setting unit 15 sets the road friction coefficient $\mu$, based on the front wheel slip angle $\alpha f$ and the self-aligning torque Ta, referring to a characteristic map, for the road friction coefficient, of the front wheel slip angle and the self-aligning torque.

According to the second embodiment, the road friction coefficient can be precisely estimated in the wide driving ranges while reducing noises of the sensors in the vehicle equipped with the electric power steering device in the same manner as the first embodiment.

According to the above described present invention, since the road friction coefficient is set based on the relationship of the self-aligning torque which operates on the steered wheel and the slip angle of the steered wheel obtained by inputting detected values of the vehicle motion state to the observer formed by the motion model of the vehicle, the road friction coefficient can be precisely estimated in the wide driving ranges with little noise of the sensor.

Having described the preferred embodiments of the invention referring to the accompanying drawings, it is to be understood that the invention is not limited to those precise embodiments and that various changes and modifications thereof could be effected by one skilled in the art without departing from the spirit or scope of the invention as defined in the appended claims.

What is claimed is:

1. A road friction coefficient estimating apparatus, comprising:
    self-aligning torque detecting means for detecting a self-aligning torque of a steered wheel;
    steered wheel slip angle detecting means for detecting a slip angle of the steered wheel by inputting a detected value of a vehicle motion parameter to an observer formed by a motion model of a vehicle; and
    road friction coefficient setting means for setting a road friction coefficient based on the relationship between the self-aligning torque and the steered wheel slip angle.

2. The road friction coefficient estimating apparatus according to claim 1, wherein the road friction coefficient setting means prohibits the setting of the road friction coefficient based on a preset vehicle speed condition.

3. The road friction coefficient estimating apparatus according to claim 1, wherein the road friction coefficient setting means prohibits the setting of the road friction coefficient based on the preset slip angle of the steered wheel.

4. A vehicle equipped with the road friction coefficient estimating apparatus according to claim 1, wherein the road friction coefficient estimated by the road friction coefficient estimating apparatus is used for one of control parameters of the vehicle.

5. A road friction coefficient estimating apparatus, comprising:
   a hydraulic power steering device for assisting a steering force by an oil pressure applied to a pair of hydraulic chambers of a power cylinder;
   oil pressure detecting means for detecting each oil pressure of the pair of hydraulic chambers;
   self-aligning torque detecting means for calculating a self-aligning torque based on a higher pressure of the pair of hydraulic chambers;
   steered wheel slip angle detecting means for detecting a slip angle of the steered wheel by inputting a detected value of a vehicle motion parameter to an observer formed by a motion model of a vehicle; and
   road friction coefficient setting means for setting a road friction coefficient based on the relationship between the self-aligning torque and the steered wheel slip angle.

6. The road friction coefficient estimating apparatus according to claim 5, further comprising:
   steering speed detecting means for detecting a steering speed, wherein the self-aligning torque detecting means corrects the self-aligning torque according to the steering speed.

7. The road friction coefficient estimating apparatus according to claim 5, wherein the road friction coefficient setting means prohibits the setting of the road friction coefficient based on a preset vehicle speed condition.

8. The road friction coefficient estimating apparatus according to claim 5, wherein the road friction coefficient setting means prohibits the setting of the road friction coefficient based on the preset slip angle of the steered wheel.

9. A vehicle equipped with the road friction coefficient estimating apparatus according to claim 5, wherein the road friction coefficient estimated by the road friction coefficient estimating apparatus is used for one of control parameters of the vehicle.

10. A road friction coefficient estimating apparatus, comprising:
    a hydraulic power steering device for assisting a steering force by an oil pressure applied to a pair of hydraulic chambers of a power cylinder;
    oil pressure detecting means for detecting each oil pressure of the pair of hydraulic chambers;
    self-aligning torque detecting means for calculating a self-aligning torque based on a difference of pressure in the pair of hydraulic chambers;
    steered wheel slip angle detecting means for detecting a slip angle of the steered wheel by inputting a detected value of a vehicle motion parameter to an observer formed by a motion model of a vehicle; and
    road friction coefficient setting means for setting a road friction coefficient based on the relationship between the self-aligning torque and the steered wheel slip angle.

11. The road friction coefficient estimating apparatus according to claim 10, further comprising:
    steering speed detecting means for detecting a steering speed, wherein the self-aligning torque detecting means corrects the self-aligning torque according to the steering speed.

12. The road friction coefficient estimating apparatus according to claim 10, wherein the road friction coefficient setting means prohibits the setting of the road friction coefficient based on a preset vehicle speed condition.

13. The road friction coefficient estimating apparatus according to claim 10, wherein the road friction coefficient setting means prohibits the setting of the road friction coefficient based on the preset slip angle of the steered wheel.

14. A vehicle equipped with the road friction coefficient estimating apparatus according to claim 10, wherein the road friction coefficient estimated by the road friction coefficient estimating apparatus is used for one of control parameters of the vehicle.

15. A road friction coefficient estimating apparatus, comprising:
    an electric power steering device for assisting a steering force with an electric motor;
    torsion bar torque detecting means for detecting a torsion bar torque;
    motor current detecting means for detecting the driving current of the electric motor;
    self-aligning torque detecting means for calculating a self-aligning torque based on the torsion bar torque and the motor current;
    steered wheel slip angle detecting means for detecting a slip angle of the steered wheel by inputting a detected value of a vehicle motion parameter to an observer formed by a motion model of a vehicle; and
    road friction coefficient setting means for setting a road friction coefficient based on the relationship between the self-aligning torque and the steered wheel slip angle.

16. The road friction coefficient estimating apparatus according to claim 15, further comprising:
    steering speed detecting means for detecting a steering speed, wherein the self-aligning torque detecting means corrects the self-aligning torque according to the steering speed.

17. The road friction coefficient estimating apparatus according to claim 15, wherein the road friction coefficient setting means prohibits the setting of the road friction coefficient based on a preset vehicle speed condition.

18. The road friction coefficient estimating apparatus according to claim 15, wherein the road friction coefficient setting means prohibits the setting of the road friction coefficient based on the preset slip angle of the steered wheel.

19. A vehicle equipped with the road friction coefficient estimating apparatus according to claim 15, wherein the road friction coefficient estimated by the road friction coefficient estimating apparatus is used for one of control parameters of the vehicle.

* * * * *